United States Patent [19]

Hinckley

[11] Patent Number: 4,833,087

[45] Date of Patent: May 23, 1989

[54] DISPOSABLE CONTAINER CONFIGURED TO PRODUCE UNIFORM SIGNAL

[75] Inventor: Charles C. Hinckley, Pittsford, N.Y.

[73] Assignee: Eastman Kodak Company, Rochester, N.Y.

[21] Appl. No.: 19,810

[22] Filed: Feb. 27, 1987

[51] Int. Cl.[4] .......... G01N 33/487

[52] U.S. Cl. .......... 435/287; 435/810; 436/807; 436/809; 422/58; 422/61; 422/101; 422/102

[58] Field of Search .......... 435/7, 5, 287, 292, 435/293, 294, 299, 300, 301, 810; 436/527, 530, 531, 548, 807, 808, 809, 810, 165; 422/58, 61, 101, 102

[56] References Cited

U.S. PATENT DOCUMENTS

| | | | |
|---|---|---|---|
| 3,550,853 | 12/1970 | Gray | 239/44 |
| 3,825,410 | 7/1974 | Bagshawe | 23/230 R |
| 3,888,629 | 6/1975 | Bagshawe | 422/61 X |
| 3,964,871 | 6/1976 | Hochstrasser | 435/805 |
| 4,189,464 | 2/1980 | Blomberg et al. | 436/809 X |
| 4,216,245 | 8/1980 | Johnsson | 422/56 X |
| 4,246,339 | 1/1981 | Cole et al. | 435/7 |
| 4,317,726 | 3/1982 | Shepel | 422/101 |
| 4,366,241 | 12/1982 | Tom et al. | 436/807 X |
| 4,407,943 | 10/1983 | Cole et al. | 435/7 |
| 4,632,901 | 12/1986 | Valkirs et al. | 436/807 X |
| 4,672,024 | 6/1987 | Giaeuer et al. | 436/810 X |
| 4,734,262 | 3/1988 | Bagshawe | 422/101 |

*Primary Examiner*—Samuel Scott
*Assistant Examiner*—Carl D. Price
*Attorney, Agent, or Firm*—Dana M. Schmidt

[57] ABSTRACT

There is disclosed a container for storing a reagent and then for reacting the reagent to produce a signal representative of the presence of an analyte, or of the amount of that analyte. The container is disposable and comprises at least one compartment having an upper portion and a lower portion. The upper portion comprises a stored reagent and means for retaining for observation on an indicator surface a reaction product of such reagent following a reaction of the reagent with a liquid sample. The lower portion includes means for absorbing liquid extracted from the upper portion through the retaining means. The absorbing means is configured with a shape that contacts the confining means only at locations spaced inwardly away from at least two of the side walls of the upper portion, whereby the reaction product of the liquid sample and the reagent is induced to flow into the confining means away from the two side walls to produce a uniform signal.

11 Claims, 1 Drawing Sheet

DISPOSABLE CONTAINER CONFIGURED TO PRODUCE UNIFORM SIGNAL

FIELD OF INVENTION

This invention relates to disposable containers that both store a reagent needed for a reaction, and provide the reaction chamber for the reaction. Particularly it relates to such containers wherein there is included means for separating the reaction product of the reaction from the liquid used for the reaction.

BACKGROUND OF THE INVENTION

Home testing is becoming an important market for diagnostic assays. Examples include home test kits for pregnancy, ovulation, & occult blood. It is common in such tests to provide a disposable device that has indicator reagents that react directly with the analyte of choice in the body fluid being tested, to produce a visual indication of the presence or absence of that analyte. As an example of the latter, immunoassays for infectious disease may require the subsequent addition of another liquid containing an appropriate label that will attach to the indicator layer and produce a detectable change, only if the analyte in question is significantly present in the body fluid.

Thus the disposable device is preferably both a storage container for at least some of the reagents involved, in dried form, and a reaction chamber to develop a visually observable change when the body fluid is added.

Examples of disposable devices that have been provided for such a use include those described in U.S. Pat. Nos. 3,825,410 and 3,888,629, issued on 7/23/74 and 6/10/75, respectively. Both of these feature a container with at least one compartment that has an upper portion and a lower portion. In the container of the '629 patent, the upper portion contains a stored reagent for reaction with the sample liquid, and a filter matrix. Preferably the reagent is stored on or in the matrix, which provides an indicator surface. The lower portion contains means for absorbing liquid from the upper portion through the filter matrix. The upper and lower portions are confined between side walls, and the absorbing means extends the full width of the side walls.

It has been found that the difficulty with such a device is that, because the absorbing means are in contact with the side walls at the place of contact with the filter matrix, the surface tension of the liquid at the side walls causes excessive amounts of solution to be drawn through the filter matrix during the absorbing step, at the walls. As a result, reaction product formed during the reaction is non-uniformly distributed, with a higher concentration at the walls.

One approach to this problem has been to fix the reagent to a prescribed central part of the filter matrix. In such a device, the reagent and the resulting reaction product cover an area having a symbolic shape, such as a plus sign or a minus sign. As a result, however, the reaction occurs only while the liquid flows through the filter matrix. That is, the reagent is not capable of floating free into free liquid above the matrix. However, if it were not so fixed to a central area, so that it could diffuse into liquid temporarily held above the matrix, thereby increasing the rate of reaction, there would be incurred the problem noted in the previous paragraph.

Therefore, prior to this invention there has been a need for a disposable container of the type described, which produces a more uniform signal at the indicator surface, without requiring that the reagent be somehow fixed just to a central area of the indicator surface.

SUMMARY OF THE INVENTION

I have discovered a container configuration which overcomes the aforedescribed dilemma.

More specifically, there is provided a disposable container for testing liquid samples for the detection of an analyte, the container comprising at least one compartment that in turn comprises an upper portion comprising (a) a stored reagent for reaction with the liquid sample within the compartment, and (b) means for retaining for observation a reaction product of such reagent on an indicator surface after the reagent reacts with the liquid sample and all liquid is withdrawn. The compartment also has a lower portion retaining means for absorbing liquid extracted from the upper portion through the retaining means, and for storing such liquid, the compartment being physically defined and limited by walls including the walls extending vertically along at least the upper portion of the compartment.

The container is improved in that the reagent is provided in a form capable of moving into free liquid disposed above the retaining means, and in that the absorbing means is configured with a shape that contacts the retaining means only at locations spaced inwardly away from at least two of the side walls, whereby the reaction product of the liquid sample and the reagent is induced to flow into the retaining means away from the two side walls to produce a more uniform signal.

Thus, it is an advantageous feature of the invention that a disposable container is provided with a stored reagent for producing a detectable signal that is uniformly distributed on an indicator surface, without requiring that the reagent be confined and bound to only certain central regions of that surface.

It is a related advantageous feature of the invention that such a container has a stored reagent that is free to diffuse into the patient sample liquid while the latter is held in the upper portion, thereby increasing the rate of reaction.

Other advantageous features will become apparent upon reference to the following description of the preferred embodiments when read in light of the attached drawings.

DESCRIPTION OF THE PREFERRED EMBODIMENTS

In the following discussion, the container of the invention is discussed primarily with regard to its use in an immunoassay, a preferred use. In addition, it is useful for any liquid reaction that is adapted to be conducted and filtered after long term storage of at least the reagent of the container. It is particularly useful to provide a qualitative indication of the presence or absence of an analyte in a patient sample liquid.

Figure 1:
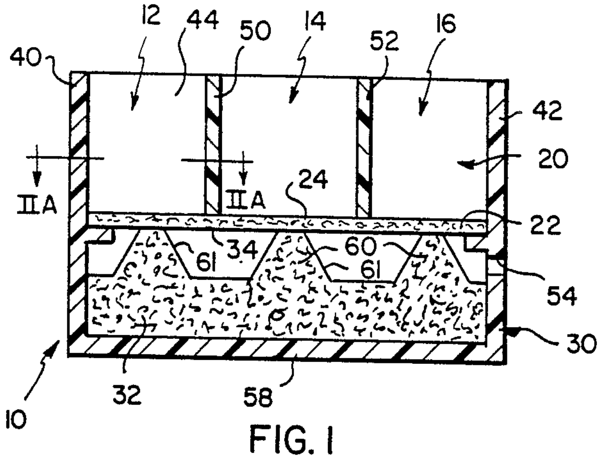
FIG. 1 is an elevational section view taken though a container constructed in accordance with the invention.

The container of FIG. 1 comprises three adjacent compartments, 12, 14 and 16. Each of these has an upper portion 20 and a lower portion 30. The upper portion comprises a retaining matrix 22 of a fibrous material, such as filter paper, cloth, porous membrane or the like, constructed to retain on that material a reaction product yet to be formed. Portion 20 also comprises at least one reagent preferably disposed on the surface 24 of matrix 22 in a form capable of allowing the reagent to move into free liquid sitting above matrix 22. Any such form is useful, for example, as by bonding the reagent to buoyant beads coated over the matrix. The beads may be bonded together initially, by a water soluble material for reasons that will become clear. Any suitable bonding material that is water soluble is useful. The choice of the reagents will depend, of course, on the preferred reaction and the analyte of choice. (As used herein, "reagent" means any substance, including an inhibiting agent, that will produce a reaction or inhibition of a reaction that will result in detectable product.)

Lower portion 30 of container 10 comprises an absorbing medium 32 that is in contact with the underside 34 of matrix 22. Preferably such medium will hold 2 mL amounts of aqueous solution. Examples of useful material for this purpose include cotton, cellulose acetate, and other synthetic fibers.

The 3 compartments 12, 14 and 16 are defined and limited by vertically extending walls 40, 42, 44, and 50 and 52. Of these, walls 50 and 52 extend vertically along only the upper portion of two adjacent compartments, while the others extend along both upper and lower portions. In one of the walls 40 & 42, a closeable aperture 54 is provided, the closure of which is not shown. This aperture by its open or closed state controls whether or not gravity flow of liquid can proceed from the upper to the lower portions of the compartments. In addition, aperture 54 can be used to pull a partial vacuum on the compartments, to assist in pulling the liquid through matrix 22.

A bottom wall 58 serves as the bottom confining wall of the container.

Figure 2A:
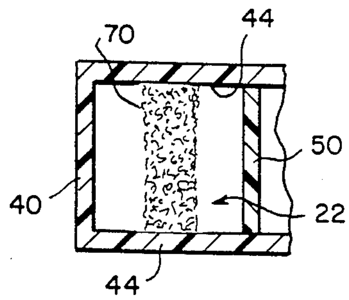
FIG. 2A is a fragmentary sectional view taken generally along the line IIA—IIA of FIG. 1.

In accord with an aspect of the invention absorbing medium 32 is constructed with a peculiar shape that ensures that it contacts underside 34 only at locations that are spaced away from walls 40 & 50, or 50 & 52, or 42 & 52, respectively, for each of the 3 compartments. As shown, tooth-shaped projections 60 are provided to medium 32 at the place of contact with underside 34 of matrix 22. The result is that as the liquid, temporarily stored in upper portion 20 to allow reaction with reagents 24, is drawn into matrix 22, the reaction product produced in the reaction flows only into the matrix portion directly overlying projections 60. Assuming the reaction product is visually observable, FIG. 2A, such as from a dye, the resulting image takes on the outline 70 of that flow-through area, with a uniform distribution of signal. There is no excessive amount at two of the side walls since flow-through does not occur at the side walls. In this particular embodiment image outline 70 is a rectangle that does extend into contact with side walls 44. In addition, a version having a shorter length of projections 60 will produce a shorter image rectangle 70, not shown, that does not extend to any side wall.

All three of compartments 12, 14 and 16 can produce the same image.

The following is a preferred example of an assay that can be run using this container: (This is subject matter invented by Brian Snyder et al and described and claimed in U.S. Ser. No. 019,850 entitled "Agglutination Immunoassay and Kit for Determination of A Multivalent Immune Species Using a Buffered Salt Wash Solution" filed on Feb. 27, 1988).

To assay for strep, an immunoreaction is available between an immobilized antibody bearing also a label and the strep antigen. This assay is carried out as follows: The antibody for the beads placed on matrix 22, as reagents 24; is AntiStrep A serum, obtained from Difco Labs (Detriot, Mich.). An IgG fraction is obtained by ammonium sulfate precipitation. The antibody is immobilized on beads comprising a copolymer of styrene, chloromethylstyrene, and hydroxyethylacrylate (69/30/1 wt/wt) and beads comprising a copolymer of styrene, chloromethystyrene, and acrylic acid (85/10/5 wt/wt). The beads are 0.7 $\mu$m in diameter, imbibed with europium chelate as the label. Nylon membrane filters made of "Nylon 66", with a 5.0 $\mu$m pore size are pretreated by incubating the filters in 0.5% instant non-fat dry milk, 50 mM Tris buffer at pH 8.0, and 100 mM NaCl for 2 hr at room temperature. The filters are then placed on a Buchner funnel and washed with 50 mM of the Tris buffer and, 100 mM NaCl (using vacuum aspiration). Ten microliters of an antibody bead solution described above are then spotted onto the filter in compartments 12, 14 & 16, FIG. 1. (Such beads float up into free liquid disposed above the membrane filters, to allow the AntiStrep A to react with strep antigen.)

In addition, Strep A extracts (of antigen) are prepared in a similar way, and added onto the coating of beads plus AntiStrep A, but only in compartment 12. For compartment 16, a solution of N-acetylglucosamine is added, as a conventional anti-agglutinating agent. (This agent functions, as is well known, to prevent agglutination of the beads plus antibody unless adverse conditions are present, for example, too much salt, or too low a pH. In these adverse condditions, the beads plus antibody of compartment 14 will agglutinate whether or not antigen is present in the patient sample, and the test has to be discarded.)

In some embodiments, it is desirable that the liquid absorbed into medium 32 not rewet filter matrix 22. To this end, a more hydrophobic cover (not shown) can be applied to surface 61 of projections 60. Suitable materials are described in U.S. Pat. No. 4,246,339, such as non-woven rayon.

Figure 2B:
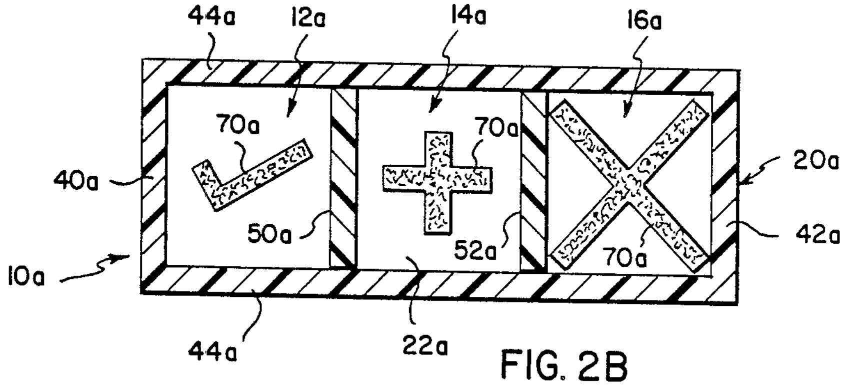
FIG. 2B is a sectional view similar to that of FIG. 2A, except it is of an entire alternative embodiment.

It is not necessary that the image, if any, produced in all three compartments be the same, or indeed, that they have any one particular shape. Highly preferred is a container wherein the images have a symbolic shape, each one being different, FIG. 2B. Parts similar to those previously described bear the same reference numeral, to which the distinguishing suffix "a" is appended.

Thus, container 10*a* comprises three adjacent compartments 12*a*, 14*a*, and 16*a* confined between side walls 40*a*, 42*a*, 44*a*, 50*a* and 52 *a* as described above, with upper portion 20*a* and a lower portion not shown. The sole difference in this embodiment is the shape of the absorbing medium in the lower portion. At the place of contact with filter matrix 22*a*, that medium has the shapes represented by the dye image 70*a* a formed in matrix 22*a* after filtering. Thus, the shape of the medium in compartment 12*a* is one of a check mark or minus sign, which symbolically indicates the absence of the analyte of choice, and is otherwise a negative control. The shape for compartment 14*a* is a plus-sign, which is the symbolic indication of the presence of the analyte of choice. The shape for compartment 16*a* is a large X, a symbolic indication that the test reaction is a failure, for example, if one of the reagents has decomposed. The shape of these images is controlled by shaping the projections, not shown, of the absorbing material underneath matrix 22a.

Figure 3:
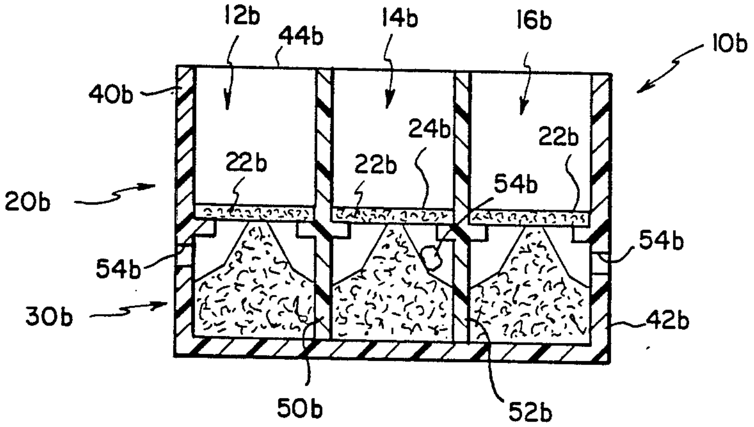
FIG. 3 is an elevational section view similar to that of FIG. 1, but of still another embodiment.

In some embodiments, it may be desirable to isolate the absorbing medium in one compartment from that of the adjacent compartments, FIG. 3. Such is particularly advantageous in reactions susceptible to cross-talk between compartments. Parts similar to those previously described bear the same reference numerals, to which the distinguishing suffix "b" is appended.

Thus, device 10b comprises three adjacent compartments 12b, 14b and 16b as described above, with upper portion 20b and lower portion 30b, containing, respectively, filter matrix 22b and reagent 24b, and absorbing medium 32b. Side walls 40b, 42b and 44b are constructed as before. Unlike the previous embodiments, however, the side walls 50b and 52b extend full height, so as to divide medium 32b into three isolated pieces. In such a construction, a vent aperture 54b is provided for each compartment, in one of the exterior side walls.

Each of the aforesaid embodiments has the advantage of allowing the reagents on matrix 22b to disperse into the liquid that is temporarily held above the matrix through the closure of the apertures in the lower portion. For example, if the reagent is coated within a water soluble polymeric matrix when the patient sample is added, within 2–5 min. much of it has dissolved or dispersed into the liquid above the matrix.

During use, the patient sample is added only to compartment 14 (or 14a, 14b). The liquid sits above the filter because vents 54 (or 54b) are kept closed. During an appropriate incubation time, the beads and their antibodies float up into the solution, since the solution dissolves the water-soluble material holding the beads on matrix 22. During this incubation, any antigen present will cause the beads and their antibodies to agglutinate (in compartment 14, FIG. 1). After that incubation period, the vents in the lower compartment are opened, and the liquid flows through matrix 22 but only at the areas in contact with medium 32.

The next step is to add plain water as a wash step to all three compartments. In compartment 12, the antigen already present as manufactured will cause agglutination and retention of the beads containing the label (such as the fluorescent chelate.) In compartment 14, the wash will wash through beads not agglutinated, which will be all of them UNLESS the patient's sample is positive. In compartment 16, no agglutination occurs unless the test fails (such as if salt water were used in the water, etc. ) An appropriate fluorimeter reader will then allow the user to detect labeled, fluorescing beads retained on the filter.

The invention has been described in detail with particular reference to preferred embodiments thereof, but it will be understood that variations and modifications can be effected within the spirit and scope of the invention.

What is claimed is:

1. In a disposable container for testing liquid samples for the detection of an analyte, the container including at least one compartment comprising an upper portion and a lower portion below said upper portion, said upper portion comprising (a) vertically extending side walls providing an access aperture at their upper end, (b) a stored reagent for reaction with a liquid sample within the compartment, and (c) porous means at an end opposite to said upper end for retaining for observation a reaction product of said reagent when liquid passes through said porous means, said porous means having an exposed, upper surface;

said lower portion comprising wall means defining a chamber and absorbing means in said chamber below said porous retaining means, for absorbing and storing all liquid passed through said porous retaining means from said upper portion, said absorbing means being in contact with said porous retaining means and configured to absorb and extract all liquid from said upper portion;

the improvement wherein said reagent is provided in a form capable of moving into free liquid disposed above said porous retaining means, and said absorbing means is configured with a shape that contacts said porous retaining means only at locations spaced inwardly away from at least two of said side walls, and not along said two side walls such that a portion of the lower surface of said porous retaining means is not in contact with a portion of said absorbing means to provide a void at predetermined locations between a portion of the absorbing means and a portion of the porous retaining means, whereby the reaction product of the liquid sample and said reagent is induced to flow into said porous retaining means where the absorbing means contacts the retaining means and away from said two side walls to produce a retention of reaction product in an isolated area.

2. A container as defined in claim 1, wherein said absorbing means is configured to contact said retaining means at locations spaced inwardly away from all of said side walls.

3. A container as defined in claim 1, wherein said lower portion includes means defining a vent aperture to vent said lower portion.

4. A container as defined in claim 1, wherein said absorbing means is configured with a shape contacting said retaining means that has a symbolic meaning, whereby the reaction product of the liquid sample and said reagent is induced to flow into said retaining means only in areas that form a visual symbol.

5. A container as defined in claim 4, wherein said shape of said absorbing means is a symbol for the presence of said analyte.

6. A container as defined in claim 4, wherein said shape of said absorbing means is a symbol for the absence of said analyte.

7. A container as defined in claim 4, wherein said shape of said absorbing means is a symbol for a failure of the test reaction.

8. In a disposable container for testing liquid samples for the detection of an analyte, the container including at least one compartment comprising an upper portion and a lower portion below said upper portion, said upper portion comprising (a) vertically extending side walls providing an access aperture at their upper end, (b) a stored reagent for reaction with a liquid sample within the compartment, and (c) porous means at an end opposite to said upper end for retaining for observation a reaction product of said reagent when liquid passes through said porous means, said porous means having an exposed, upper surface;

said lower portion comprising wall means defining a chamber and absorbing means in said chamber below said porous retaining means, for absorbing and storing all liquid passed through said porous retaining means from said upper portion, said absorbing means being in contact with said porous retaining means and configured to absorb and extract all liquid from said upper portion;

the improvement wherein said reagent is provided in a form capable of moving into free liquid disposed above said porous retaining means, and said absorbing means is configured with a shape that contacts said porous retaining means only at locations spaced inwardly away from at least two of said side walls, and not along said two side walls such that a portion of the lower surface of said porous retaining means is not in contact with a portion of said absorbing means to provide a void at predetermined locations between a portion of the absorbing means and a portion of the porous retaining means, whereby the reaction product of the liquid sample and said reagent is induced to flow into said porous retaining means where the absorbing means contacts the retaining means and away from said two side walls to produce a retention of reaction product in an isolated area;

and further including two additional compartments disposed adjacent said one compartment, said additional compartments each comprising an upper portion and a lower portion as defined for said at least one compartment, wherein said absorbing means of said additional compartments is configured with a shape that (i) is different for each of said compartments and (ii) contacts said porous retaining means only at locations spaced inwardly away from at least two of said side walls, and not along said two side walls such that a portion of the lower surface of said porous retaining means is not in contact with said absorbing means to provide a void at predetermined locations, whereby the reaction product of the liquid sample and said reagent is induced to flow into said porous retaining means of each of said additional compartments away from said two side walls of said each compartment.

9. A container as defined in claim 8, wherein said different shapes, at said place of contact, are individually indicative of the presence of said analyte, the absence of said analyte, and that the test is a failure.

10. A container as defined in claim 8, wherein at least one of said different shapes is two intersecting lines.

11. In a disposable container for testing liquid samples for the detection of an analyte, the container including at least one compartment comprising an upper portion and a lower portion below said upper portion, said upper portion comprising (a) vertically extending side walls providing an access aperture at their upper end, (b) a stored reagent for reaction with a liquid sample within the compartment, and (c) porous means at an end opposite to said upper end for retaining for observation a reaction product of said reagent when liquid passes through said porous means, said porous means having an exposed, upper surface;

said lower portion comprising wall means defining a chamber and absorbing means in said chamber below said porous retaining means for absorbing and storing all liquid passed through said porous retaining means from said upper portion, said absorbing means being in contact with said porous retaining means and configured to absorb and extract all liquid from said upper portion;

the improvement wherein said reagent is provided in a form capable of moving into free liquid disposed above said porous retaining means, and said absorbing means is configured with a shape that contacts said porous retaining means only at locations spaced inwardly away from at least two of said side walls, and not along said two side walls, such that a portion of the lower surface of said porous retaining means is not in contact with a portion of said absorbing means to provide a void at predetermined locations between a portion of the absorbing means and a portion of the porous retaining means, whereby the reaction product of the liquid sample and said reagent is induced to flow into said porous retaining means where the absorbing means contacts the retaining means and away from said two side walls to produce a retention of reaction product in an isolated area, and further including two additional compartments disposed adjacent said one compartment, said additional compartments each comprising an upper portion and a lower portion as defined for said at least one compartment, said absorbing means of each of said additional compartments being (i) isolated from each other by separating walls in said lower portions of said compartments, and (ii) in contact with said porous retaining means only at locations spaced inwardly away from at least two of said side walls, and not along said two side walls such that a portion of the lower surface of said porous retaining means is not in contact with said absorbing means to provide a void at predetermined locations, whereby the reaction product of the liquid sample and said reagent is induced to flow into said porous retaining means of each of said compartments away from said two side walls of said each compartment.

* * * * *